(12) United States Patent
Wappenschmidt et al.

(10) Patent No.: US 10,617,807 B2
(45) Date of Patent: Apr. 14, 2020

(54) ROTARY-PISTON PUMP

(71) Applicant: RHEINISCH-WESTFÄLISCHE TECHNISCHE HOCHSCHULE AACHEN, Aachen (DE)

(72) Inventors: Johannes Wappenschmidt, Aachen (DE); Andreas Goetzenich, Aachen (DE); Ruediger Autschbach, Aachen (DE); Ulrich Steinseifer, Hauset (BE)

(73) Assignee: RHEINISCH-WESTFAELISCHE-TECHNISCHE HOCHSCHULE AACHEN, Aachen (DE)

( * ) Notice: Subject to any disclaimer, the term of this patent is extended or adjusted under 35 U.S.C. 154(b) by 177 days.

(21) Appl. No.: 15/308,488

(22) PCT Filed: Jul. 9, 2015

(86) PCT No.: PCT/EP2015/001411
§ 371 (c)(1),
(2) Date: Jan. 2, 2017

(87) PCT Pub. No.: WO2016/012082
PCT Pub. Date: Jan. 28, 2016

(65) Prior Publication Data
US 2017/0189593 A1 Jul. 6, 2017

(30) Foreign Application Priority Data

Jul. 23, 2014 (DE) .................. 10 2014 010 745

(51) Int. Cl.
*A61M 1/10* (2006.01)
*H02K 3/28* (2006.01)
(Continued)

(52) U.S. Cl.
CPC ............. *A61M 1/1081* (2013.01); *F04C 2/22* (2013.01); *H02K 1/182* (2013.01); *H02K 3/28* (2013.01);
(Continued)

(58) Field of Classification Search
CPC ............. A61M 1/1081; A61M 1/1036; A61M 1/1029; A61M 1/1055; F04C 15/008;
(Continued)

(56) References Cited

U.S. PATENT DOCUMENTS 2,557,879 A * 6/1951 Maldwyn .............. F04C 15/008
310/66
4,551,073 A 11/1985 Schwab
(Continued)

FOREIGN PATENT DOCUMENTS

DE 102011005831 A1 * 9/2012 .............. F01C 21/10

*Primary Examiner* — Nathan C Zollinger
(74) *Attorney, Agent, or Firm* — Andrew Wilford

(57) ABSTRACT

The invention relates to a rotary piston pump, in particular for pumping blood, comprising a piston rotor (1) which has particularly two or three faces when seen in cross-section, which is mounted in a piston chamber (2) and eccentrically rotates, the piston rotor (1) having in its interior a plurality of magnetically interacting elements (4, 4a, 4b), in particular permanent magnets and/or coils, and being driven by the magnetic interaction of these elements (4, 4a, 4b) with at least one moving magnetic field.

4 Claims, 4 Drawing Sheets

(51) Int. Cl.
  *H02K 1/18* (2006.01)
  *F04C 2/22* (2006.01)
  *H02K 1/27* (2006.01)

(52) U.S. Cl.
  CPC .. *F04C 2210/1016* (2013.01); *F04C 2240/10* (2013.01); *H02K 1/2713* (2013.01)

(58) Field of Classification Search
  CPC .... F04C 15/0069; F04C 2/22; F04C 2240/10; F04C 2210/1016; F04C 2210/42; F04C 2270/11; F02B 2053/005; F01C 1/22; H02K 1/182; H02K 1/2713; H02K 3/28
  USPC .............................. 310/266, 268, 254.1, 112
  See application file for complete search history.

(56) References Cited

U.S. PATENT DOCUMENTS

| | | | | |
|---|---|---|---|---|
| 4,758,132 | A | * | 7/1988 | Hartwig .................... F01C 1/16 310/67 R |
| 5,046,932 | A | * | 9/1991 | Hoffmann ............... F04C 18/10 418/101 |
| 5,145,329 | A | * | 9/1992 | Zumbusch ........... F02M 37/041 417/356 |
| 5,391,067 | A | * | 2/1995 | Saunders .................. F01C 1/22 418/125 |
| H001966 | H | * | 6/2001 | Henry, IV ..................... 417/356 |
| 2006/0039815 | A1 | * | 2/2006 | Chertok ............... F02M 37/045 418/61.3 |
| 2008/0166251 | A1 | * | 7/2008 | Williamson ........... F01C 21/108 418/19 |

\* cited by examiner

ROTARY-PISTON PUMP

CROSS REFERENCE TO RELATED APPLICATIONS

This application is the US-national stage of PCT application PCT/EP2015/001411 filed 9 Jul. 2015 and claiming the priority of German patent application 102014010745.0 itself filed 23 Jul. 2014.

FIELD OF THE INVENTION

The invention relates to a rotary-piston pump, in particular for supplying blood, including a piston rotor driven to rotate eccentrically in a piston chamber. Such a rotary-piston pump of the kind that is the subject of the invention can, for example, function in accordance with the principle of rotary piston engines in which only the piston rotor is moved and the piston chamber is stationary.

BACKGROUND OF THE INVENTION

In such a rotary-piston pump, the piston rotor can for example be embodied as having multiple lobes, in particular two or three lobes, with the cross-section of the piston chamber viewed perpendicular to the axis of the rotary-piston pump being adapted to the eccentric trajectory of the piston rotor.

To achieve this, the piston rotor can, for example, be formed as trochoidal and the cross-section of the piston chamber or the shape of the surface that faces the piston rotor constitutes the corresponding envelope to this trochoid. Similarly, the cross-section of the piston chamber or the surface shape can describe a trochoid and the cross-section of the piston rotor constitutes the corresponding envelope.

In the present description of the invention, the term "central" refers to a position coaxial to or on the central axis of the piston chamber. The term "eccentric" is thus understood to be a position next to the central axis of the piston chamber.

Rotary-piston pumps of the above-mentioned design are generally known in the prior art, even in the blood supply field, for example in the form of an artificial heart. For example, DE 3317156 [U.S. Pat. No. 4,551,073] discloses a blood pump of this kind.

In a conventional embodiment, the rotary motion of the piston rotor in such a rotary-piston pump is transmitted with the aid of an eccentric. In this connection, according to the known prior art, the piston rotor is guided in its trajectory in the piston chamber with the aid of a gear transmission.

According to the known prior art, the mechanical components of the eccentric, in particular of the gear train, are medium-contacted, i.e. are in contact with the conveyed fluid such as blood or alternatively, seals are required to achieve a separation of the mechanical components from the conveyed fluid. Up to this point, however, the medium contact or the strict requirements with regard to tightness over time constitute as yet unsolved problems in such rotary-piston pumps.

Particularly when such rotary-piston pumps are used as blood pumps, the contact of the moving eccentric components of the prior art with the blood or a lack of tightness constituted significant problems since this can cause blood clots and can thus involve a risk of thrombosis. Blood deposits that are produced, for example despite seals that are used, can also result in a failure of the pump itself.

OBJECT OF THE INVENTION

An essential object of the invention, therefore, is to create a rotary-piston pump of the type mentioned above in which the driving components and preferably also the driven ones—preferably all of the elements that drive and guide the moving parts—aside from the piston rotor itself, have no medium contact, in particular therefore no contact with blood, and thus a hermetic sealing of the pump components is produced relative to the pumped fluid, in particular blood.

SUMMARY OF THE INVENTION

This object is attained according to the invention in that the piston rotor has a plurality of internally mounted magnetically attractable elements and is driven by magnetic interaction of these elements with at least one moving magnetic field. These magnetically attractable elements inside the piston rotor can, for example, be permanent magnets and/or coils.

In this case, the invention can preferably provide that the cross-section of the piston rotor perpendicular to the central axis has a hypotrochoid shape and the cross-section of the piston chamber or the shape of the surface constitutes the corresponding envelope, particularly taking into account a gap-forming offset. The invention, however, is not limited to this preferred embodiment.

Particularly when used as a blood pump, the invention can also provide that the piston chamber does not just have one inlet and outlet, but instead has two pairs of inlets and respective outlets can for example be provided between each of the two circulatory systems of the body. In the rotary-piston pump according to the invention, seals can for example be gap seals in/against the element that constitutes the envelope, in this case preferably the inner surface of the piston chamber. Two stationary gap seals between the housing and piston rotor thus make it possible, for example, to separate the two circulatory systems from each other.

In one embodiment, rotary motion of the piston rotor along an eccentric trajectory about the piston chamber central axis is produced exclusively by the magnetic interaction of these above-mentioned elements with the at least one magnetic field. Another embodiment can ensure that the rotated eccentric motion is indeed initiated by the magnetic interaction, but the eccentrically rotating motion is in turn subject to a compulsory guidance, for example by a mechanical eccentric support of the piston rotor in the piston chamber that is preferably also magnetic.

Such a preferably magnetic, eccentric support of the piston rotor, in order to define the eccentric trajectory of the piston rotor, can be implemented, for example, by the fact that the piston rotor has such a support on least at one of its axial end faces, preferably on the two opposite ends.

This has the advantage that such a support can take place at the axial end face and also not in medium-contacted regions of the pump, i.e. outside such regions between the inner surface of the piston chamber and the outer circumferential surface of the piston rotor that are each in contact with the medium being supplied, for example blood.

For example, either seals can be provided for this purpose between axial end faces of the piston chamber and axial end faces of the piston rotor or the mutually opposing axial flat regions of the piston rotor and piston chamber have such a small amount of movement play that the supplied medium such as blood does not pass through these small gaps.

Another possibility can provide that in the region between the axially opposing flat regions of the piston rotor and piston chamber, there is a secondary flow of the supplied medium such as blood. A secondary flow can alternatively or additionally also take place through the above-mentioned magnetically acting support of the piston rotor.

According to one possible embodiment of the rotary-piston pump the at least one moving magnetic field is produced outside the piston chamber, for example in that this at least one produced magnetic field acts through the walls delimiting the piston chamber, for example axial or also radial walls and thus interacts with the magnetically attractable elements in the piston rotor.

The movement of the at least one produced magnetic field therefore causes the magnetically attractable elements of the piston rotor, due to the attraction or repulsion forces acting between them and due to the at least one produced magnetic field, to be carried along with the movement of the magnetic field and, as a result, the piston rotor rotates eccentrically about the piston chamber central axis.

To accomplish this, at least one moving magnetic field can move eccentrically about the central axis of the piston chamber and thus the piston rotor with its plurality of magnetically attractable elements situated thereon executes this eccentric motion the same way.

In such a case, the plurality of magnetically attractable elements inside the piston rotor is preferably fixed in the piston rotor, in particular rotationally fixed.

According to another embodiment the at least one moving magnetic field—regardless of the location in which it is produced, for example outside the piston chamber—executes a motion centered on the piston chamber central axis and this concentric motion is transmitted to the plurality of magnetically attractable elements of the piston rotor that are, however, supported so that they can rotate centrally in the piston rotor in such an embodiment. As a result, the centered movement of the magnetically attractable elements about the piston chamber central axis is converted into an eccentric motion of the piston rotor in the piston chamber by eccentrically supporting these elements relative to the piston rotor.

One possible—in particular stationary—arrangement of the magnetically attractable elements in the piston rotor can occur for example in that these elements are in the vicinity of the ends of the lobes of the piston rotor. In this connection, a plurality of coils alternatingly energizable in order to produce the moving magnetic field can be positioned angularly around the outside of the inner surface of the piston chamber, with the above-described magnetically attractable elements of the piston rotor and the coils being situated radially opposite one another (relative to the central axis of the piston chamber) and the magnetic attraction or repulsion between them therefore occurring essentially radially.

An alternating energization of the coils arranged angularly therefore causes the magnetic field to move angularly around the piston chamber and the magnetic, in particular attracting interaction, causes the magnetically attractable elements such as permanent magnets in the piston rotor to also move in the movement direction of the magnetic field.

Preferably, it is possible here to provide that—particularly in order to avoid an axial tilting of the piston rotor in the piston chamber—the magnetically attractable elements and the energizable coils are arranged in at least two respective groups spaced from each other axially, with each group of magnetically attractable elements being associated with a respective group of energizable coils in terms of the magnetic interaction. In this case, the groups can preferably be positioned in the vicinity of the respective axial end faces of the piston rotor and piston chamber.

With such a placement exclusively at the axial end faces, it is thus possible to provide for example only two groups.

This embodiment particularly includes implementation of the above-described embodiment in which the at least one moving magnetic field is produced outside the piston chamber, namely radially outside the inner surface of the piston chamber relative to the central axis of the piston chamber by the coils positioned there. The at least one moving magnetic field acts through this inner surface of the piston chamber to interact with the magnetically attractable elements of the piston rotor. Consequently, this embodiment clearly demonstrates that there is no medium contact, in particular no contact of blood, with the drive components of such a rotary-piston pump.

Two other embodiments described below can provide that the magnetically attractable elements are in the piston rotor, in particular in elements that are fixed therein, in the vicinity of at least one axial end face, particularly in or under an axial end face of the piston rotor. The magnetic field lines of these elements thus preferably pass through essentially the axial end face of the piston rotor and/or the piston chamber.

According to a first possible embodiment, a plurality of coils alternatingly energizable to produce the moving magnetic field can be spaced axially from the elements of the piston rotor behind an axial end wall of the piston chamber; for example, these coils are in the piston rotor in accordance with the shape, the surface of the piston chamber (if need be shifted by an offset), or in accordance with the trajectory of the magnetically attractable elements, particular in a manner that overlaps the trajectory in the latter case.

Thus if these coils are then energized in alternating fashion, the at least one moving magnetic field travels preferably in the same way as the magnetically attractable elements; in this case, however, magnetic attraction forces or repulsion forces between the coils and the elements of the piston rotor are directed axially in comparison to the embodiment mentioned above, with the placement of the coils outside the surface of the piston chamber, with the action being exerted in an essentially radial direction.

An improved axial positional stability of the piston rotor in the piston chamber is particularly achieved with an axial, two-ended design of this above-mentioned embodiment. It is also possible—in this embodiment, but also in all of the other embodiments with energized coils for implementing the drive—to actively control the coil currents in order to stabilize the position, for example the axial and/or radial position or angular position of the piston rotor in the piston chamber.

Another embodiment in connection with the positioning of the magnetically attractable elements in the piston rotor in the vicinity of at least one axial end face, particularly in or under an axial end face thereof, can provide that behind an axial end wall of the piston chamber, in particular such a wall that is thus at least partially contacted by medium on the inside, a plurality of permanent magnets is positioned spaced axially from the magnetic elements of the piston rotor on a rotatable rotor that is driven or at least can be driven by a motor.

As a result, driving such a rotor by a motor can therefore produce a moving magnetic field that acts through the axial end wall of the piston chamber into the inside of the piston chamber and therefore on the magnetic elements of the piston rotor, consequently also driving the piston rotor exclusively by magnetic interaction.

Here, too, it is clear that the mechanical components of the drive, in this case the rotating rotor with permanent magnets, have no contact with the medium since this rotor is located outside the piston chamber, for example behind an axial end wall of the piston chamber.

With a stationary arrangement of the magnetically attractable elements in the piston rotor, it can in this case be provided that the rotatable rotor rotates eccentrically relative to the central axis of the piston chamber so that the eccentric motion of this rotor is transmitted to the piston rotor. The eccentric rotation of the rotor or also of other elements described in the context of this invention is understood to mean that the element in question rotates on itself, in particular about its own center of gravity and in particular, this center of gravity revolves about the central axis of the piston chamber, i.e. two rotary motions overlap each other.

Such a rotor can alternatively also be arranged so that it rotates centrally about the central axis of the piston chamber. In such an embodiment, however, the magnetically attractable elements of the piston rotor are rotatably supported in the latter on an eccentric; in other words, the eccentric supporting these elements executes a rotating motion centered on the piston chamber central axis and because of its eccentric shape and eccentric support in the piston rotor, then forces the latter along an eccentric trajectory.

As already mentioned above, in each of the embodiments discussed above and also in the embodiments to be discussed below, the piston rotor can be supported in an eccentrically rotatable fashion, in particular is supported magnetically, on at least one of its axial end faces, preferably on both axial end faces.

Such a support can, for example, be a first magnetic or at least magnetizable ring that is fastened centrally to an axial piston chamber wall and whose ring center thus lies on the centric piston chamber central axis, and a second magnetic or at least magnetizable ring that is positioned eccentrically at the axial end face in the piston rotor and whose ring center is thus positioned next to the piston chamber central axis; with the rotation of the piston rotor, this second ring rolling with its inner ring surface against the outer ring surface of the first ring with a magnetically attracting interaction directly or indirectly via a material positioned between the ring surfaces, in particular a magnetizable material. Such an interposed material can, for example, form pole shoes, in particular blood-compatible pole shoes. In this case, mechanical processing of this material makes it possible to improve the rolling properties of the rings. In all of the possible embodiments, the interposed material can also be formed as a coating of at least one of the mutually opposed ring surfaces.

A magnetically attracting interaction between the inner and outer ring surface of these two above-mentioned rings can, for example, be implemented in that one, preferably both, of the rings are each magnetized in alternating fashion angularly so that, viewed radially during the rolling process, attracting polarities of the ring magnetization are situated opposite one another. In this way, a kind of magnetic gear, as it were, is implemented in which angularly, north and south poles come into magnetic engagement with one another in respectively alternating fashion. Such a design can effectively prevent the rings from slipping relative to each other.

Another embodiment can also provide that at least one, preferably both, of the rings have a magnetic polarity radially that is constant angularly, i.e. with the north pole on the radial inside, for example, and the south pole on the radial outside, so that with such a placement, viewed angularly, the two same opposite polarities are always rolling against each other. It is also possible to use axially magnetized rings.

With regard to the embodiments with the two rings mentioned above, it should be noted that it is in fact preferable for both rings to be magnetized, but for the effect according to the invention, it is sufficient if one of the rings is magnetized and the other is merely magnetizable.

The rolling of the inner and outer ring surfaces of the two above-mentioned rings thus forcibly guides the piston rotor in its eccentric motion so that movement of the piston rotor caused by the at least one moving magnetic field is not subject to any risk of an axial tilting or undesirable radial shifting.

As already mentioned above, the preferred axial end face location of the support, particularly in a recess in an axial end face of the piston rotor, makes it basically possible for this support to have no contact with the medium so long as the supplied medium such as blood cannot pass through the axial gap between the piston rotor and piston chamber wall, which can be achieved, for example, by appropriately small gap dimensions or by use of additional seals.

The supplied medium such as blood can also circulate around these rings as an alternative to the formation of a secondary flow that has already been described above. In such a case, sealing measures can be omitted, which simplifies the design and is a more fail-safe embodiment. In this case, the above-mentioned support embodiment is particularly advantageous because only linear contact is produced between the rings during the rolling and thus no damage to the blood is to be expected.

According to another embodiment the magnetically attractable elements are positioned in an eccentric supported in the piston rotor so that it is able to rotate centrally relative to the piston chamber central axis. This embodiment focuses on the fact that in order to drive the piston rotor, the at least one moving magnetic field executes a motion centered on the piston chamber central axis, the magnetically attractable elements of the piston rotor are thus carried along with this coaxial motion, and the eccentric motion of the piston rotor is produced by virtue of the fact that the eccentric is supported in the piston rotor so that it is able to rotate centrally about the piston chamber central axis. The eccentricity of this eccentric, in its centrally rotating motion, is thus transmitted to the motion of the piston rotor.

Both in this embodiment and in all of the other possible embodiments, the plurality of magnetically attractable elements of the piston rotor, if they are embodied as permanent magnets, can be composed of a permanent magnet ring that is multiply magnetized in alternating fashion angularly.

For the invention, therefore, the same effect is achieved whether a plurality of individual permanent magnets, particularly in a circular arrangement, is positioned in the piston rotor, particularly in or under an axial end face of the piston rotor or whether instead, an annular permanent magnet with such a magnetization that alternates angularly is used.

As with the above-mentioned rotors for producing moving magnetic fields, instead of individual, for example circularly arranged, permanent magnets, it can also be possible in this context to use a permanent magnet ring that has this above-described magnetization with the polarity that alternates multiple times angularly.

In connection with such an eccentric that is supported so that it can rotate centrally inside the piston rotor, the at least one moving magnetic field can also be produced inside the piston rotor and in this case, for example, acts through at least one wall of the piston rotor surrounding the eccentric.

Generation of the at least one magnetic field inside the piston rotor can also take place in such a way that the components producing the magnetic field are situated outside the piston chamber that encloses the supplied medium, which can happen, for example, by virtue of the fact that at least one rotor with permanent magnets that are moved thereon—embodied individually or in the form of a ring—is positioned so that it projects from an axial end wall of the piston chamber into the piston rotor.

For example, the eccentric can be positioned in the piston rotor centrally relative to the axial length of the piston rotor and on at least one side of the eccentric, preferably on both sides of the eccentric, more preferably behind an axial wall of the piston rotor, this piston rotor having an inner recess in which a rotor that can be centrally rotated by a motor is situated that has a plurality of permanent magnets spaced axially from the magnetically attractable elements of the piston rotor.

According to this embodiment the axial end face of the piston rotor, preferably at both axial end faces, is juxtaposed with a magnetic support in accordance with the above-mentioned embodiment. For example, this embodiment can also provide that the rotation shaft of the at least one rotatable rotor extends through the first magnetic or at least magnetizable ring of a magnetic support of the piston rotor, which ring is fastened centrally to an axial piston chamber wall.

Alternatively, on one axial side of the piston rotor, preferably on both axial sides, there can be axially projecting drive elements that support the magnetically attractable elements, in particular permanent magnets, and enclose these in recesses in the piston chamber. Respective driven rotors can then be situated behind axial wall regions of these recesses in the piston chamber.

Here, too, the magnetically attractable elements on the piston rotor can be stationary and the rotors are rotated eccentrically or conversely, that the rotors rotate centrally and the magnetically attractable elements in the piston rotor are positioned on an eccentric so that they can rotate eccentrically, as described above with the preferably central placement of an eccentric

BRIEF DESCRIPTION OF THE DRAWING

The possible embodiments of the rotary-piston pump according to the invention will be discussed below with reference to the figures. Therein.

SPECIFIC DESCRIPTION OF THE INVENTION

Figure 1A:
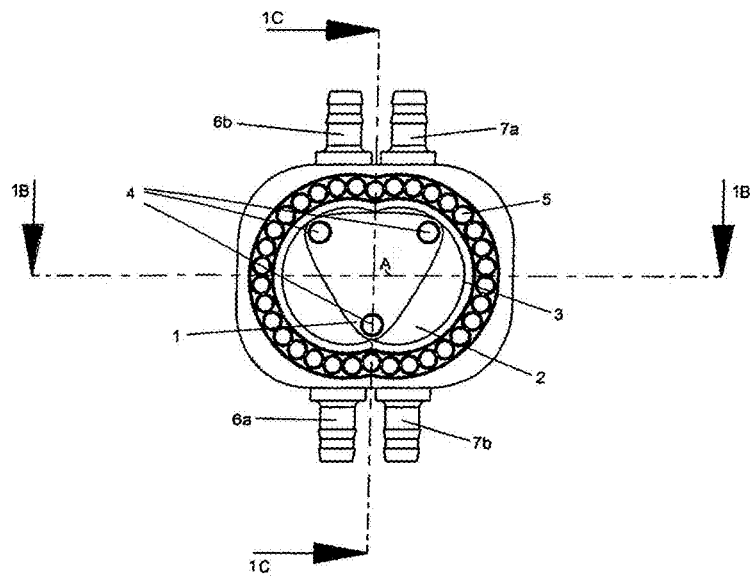
FIG. 1A is a section taken along line 1A-1A of FIG. 1B of a pump according to the invention.
Figure 1B:
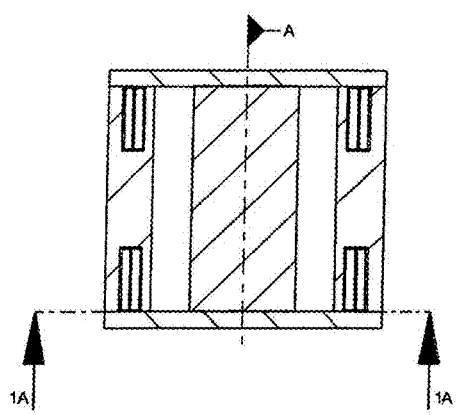
FIGS. 1B and 1C are sections taken along respective lines 1B-1B and 1C-1C of FIG. 1A.
Figure 1C:
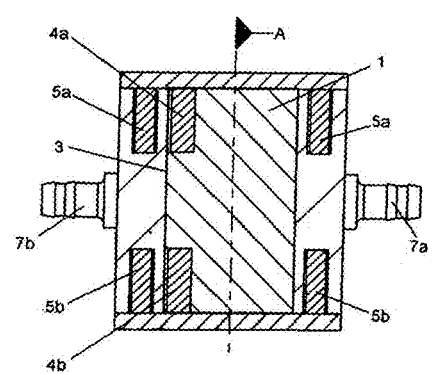
Figure 2A:
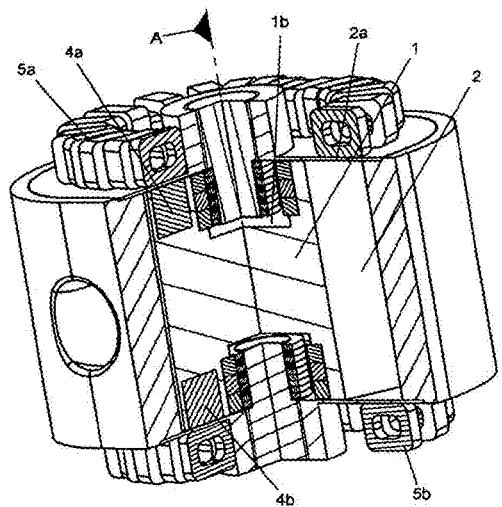
FIG. 2A is a perspective sectional view taken along line 2A-2A of FIG. 2D.
Figure 2B:
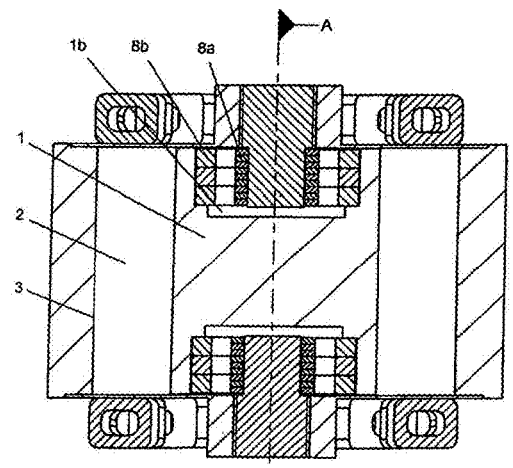
FIGS. 2B and 2C are sections taken along respective lines 2B-2B and 2C-2C of FIG. 2D.
Figure 2C:
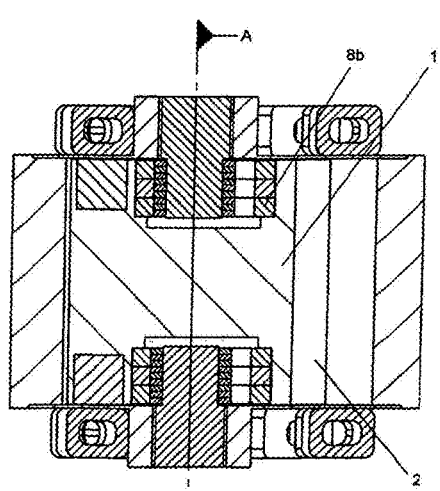
Figure 2D:
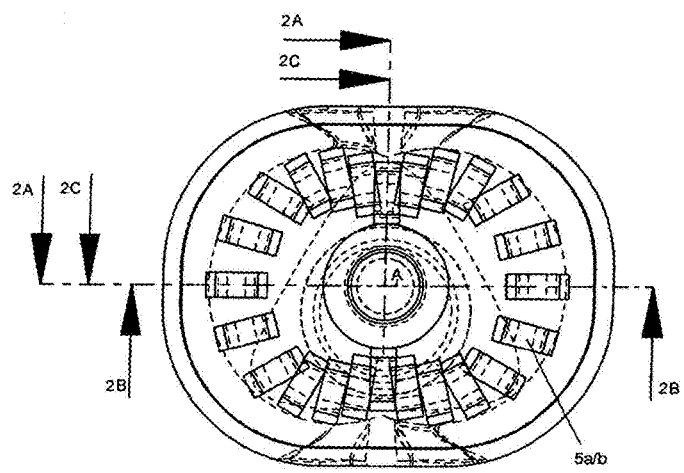
FIG. 2D is an axial end view of the pump of FIGS. 2A-2C.

In a plurality of views, FIGS. 1A-C show a first embodiment of a rotary-piston pump according to the invention.

The piston pump has a three-lobe piston rotor 1 that is rotated eccentrically about a central axis A of a piston chamber 2.

The piston rotor is formed as a hypotrochoid. The piston chamber 2 here, in cross-section perpendicular to its central axis A, has the shape of the associated envelope. The shape of the inner surface 3 of the piston chamber 2 thus also corresponds to this envelope, particularly taking into account an offset from the mathematically calculated envelope in order to form a gap between the piston rotor and the piston chamber.

In this case, the piston rotor 1, which is referred to as three-lobe, is essentially a triangular shape with rounded corners and slightly bulging faces. The cross-sectional form perpendicular to the central axis A of the piston chamber preferably corresponds to the above-mentioned hypotrochoid.

The embodiment in FIGS. 1A-C has no additional support of the piston rotor 1, i.e. it is basically able to move freely inside the piston chamber 2 with respect to rotation.

The eccentric rotary motion or revolving motion of the piston rotor here is the result of a magnetic coupling between the piston rotor 1 and at least one magnetic field produced outside the piston chamber 2. To this end, according to the invention, a plurality of electrically magnetically attractable elements 4, namely permanent magnets 4 in this case, is embedded in the piston rotor 1 each at a radially outer end of respective one of the three lobes of the three-lobe piston rotor. In other words, these elements are essentially positioned close to the rounded corners of the triangular shape.

A plurality of coils spaced angularly around the central axis A of the piston chamber 2 can be energized in alternating fashion so that the alternating energization of the individual coils 5 creates one or a plurality of magnetic field that orbit around the piston chamber.

Preferably in this case, an appropriate energization of the individual coils 5 causes the coils 5 to magnetically interact with the magnetically attractable elements 4 of the piston rotor—in other words in this case, three coils 5 or coil groups each enter into a magnetic interaction with a respective one of the three elements 4—and in particular through an attracting magnetic interaction or alternatively through a repulsing magnetic interaction, an eccentric rotation of the piston rotor 1 is produced.

The sectional views from the left side in the direction of the central axis A of the piston chamber 2 also show that inside the piston rotor 1, two groups of magnetically attractable elements 4 are provided, namely elements 4a of the first group and elements 4b of the second group, with the elements of these two different groups being spaced apart axially of the central axis A of the piston chamber 2, preferably with these elements being provided positioned in the respective axial end faces of the piston rotor 1.

In radial opposition, correspondingly energizable coils 5a and 5b, respectively, are also positioned at the axial end faces of the piston chamber, spaced angularly around the piston chamber, i.e. following the envelope. Here as well, this therefore yields two groups of coils, with each group of magnetically attractable elements 4 of the piston rotor being associated with exactly one group of coils 5, thus in this case, there is an association between the elements 4a and the coils 5a and between the elements 4b and the coils 5b.

The positioning of the two groups at the axial end faces makes it possible to ensure that the piston rotor is subjected to no axial tilting or at least no significant axial tilting during its eccentric rotation.

FIGS. 1A-C also show that the rotary-piston pump described here can perform two separate functions, namely on the one hand, a pump function between an inlet 6a and outlet 6b and on the other hand, a pump function between the inlet 7a and the outlet 7b. Such a division is particularly advantageous in the use as a heart pump since it is thus possible to implement separate pulmonary and systemic circulations. This division, however, is not compulsory; it is also possible to set up a rotary-piston pump for supplying any media, for example also blood, with only one pump inlet and one pump outlet. The corresponding implementations essentially depend on the specific cross-sectional shapes of the piston rotor and piston chamber. In an embodiment of the piston rotor with only two lobes, a rotary-piston pump according to the invention will therefore have only one inlet and one outlet. For example, it is possible to use a pump of this kind to support only a systemic circulation or alternatively, two such pumps are used.

FIG. 2 shows an alternative embodiment of the rotary-piston pump according to the invention in which magnetically attractable elements 4a and 4b are each once again positioned in the above-mentioned group arrangement at the axial end faces of the piston rotor 1; in this case, each group—as in the preceding embodiment—preferably has a number of magnetically attractable elements that corresponds to the number of lobes of the piston rotor. In this case, the magnetically attractable elements 4a and 4b can, for example, be positioned in recesses in the axial end faces of the piston rotor.

One possible variant, which is not however shown here, can also have axial permanent magnets in the flanks of the piston rotor, in particular three magnets at the ends of the lobes and three magnets interleaved with these magnets, preferably at the narrowest point between the outer wall of the piston rotor and the annular magnet of the piston rotor.

Outside the piston chamber, which is sealed off from the outside by axial end walls 2a, there is a plurality of coils 5, in this case once again in group arrangements, i.e. coils 5a in a first group and coils 5b in a second group, with the two groups on the two axially opposite end walls of the piston chamber. This therefore produces an axial spacing between the coils and the magnetically attractable elements of the piston rotor in comparison to the radial spacing of the embodiment according to FIGS. 1A-C.

In this case, the individual coils 5a and 5b are positioned in such a way that this positioning essentially follows the envelope of the trochoidal piston rotor and overlaps the trajectory of the respective magnetically attractable elements 4a and 4b. This means that an optimal axial opposition is produced between each magnetically attractable element 4a and 4b of the piston rotor and the respective coils at each position of the eccentric rotary motion of the piston rotor.

The embodiment in FIGS. 2A-D also show that, at both axial end faces of the rotary-piston pump according to the invention, the piston rotor 1 also has a support that forcibly guides the eccentric motion of the piston rotor 1. In this case, this support comprises a first permanent magnet ring 8a centered on the central axis A of the piston chamber and a second ring 8b eccentric to the axis A, particularly so that during a rotation of the piston rotor 1, the inner ring surface of the outer ring 8b rolls directly or indirectly against the surface of the inner ring 8a with a magnetically attracting action.

In this case, the inner ring 8a positioned centrally with its ring center on the axis A, is fastened to a centrally positioned journal on the axial piston chamber wall 2a and projects into an inner recess 1b on the respective axial end face of the piston rotor 1. The outer eccentrically positioned ring 8b, whose center thus lies radially next to the axis A, is fastened in the recess 1b of the piston rotor 1.

Figure 3A:
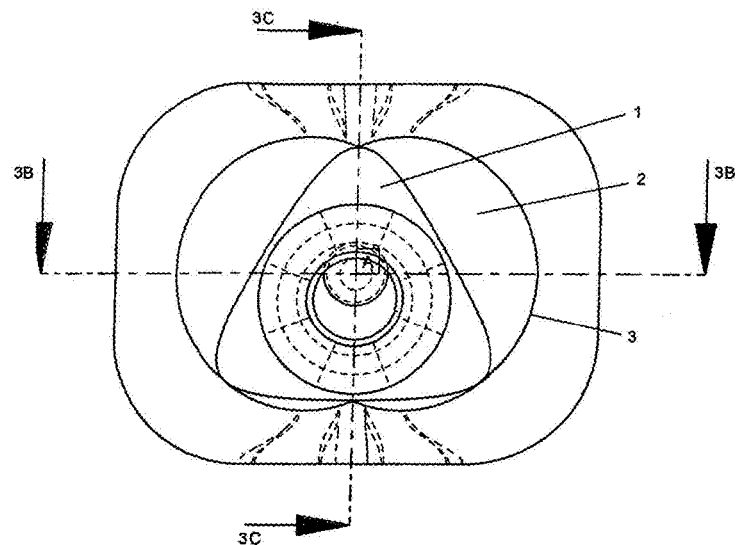
FIG. 3A is a section taken along line 3A-3A of FIG. 3B.
Figure 3B:
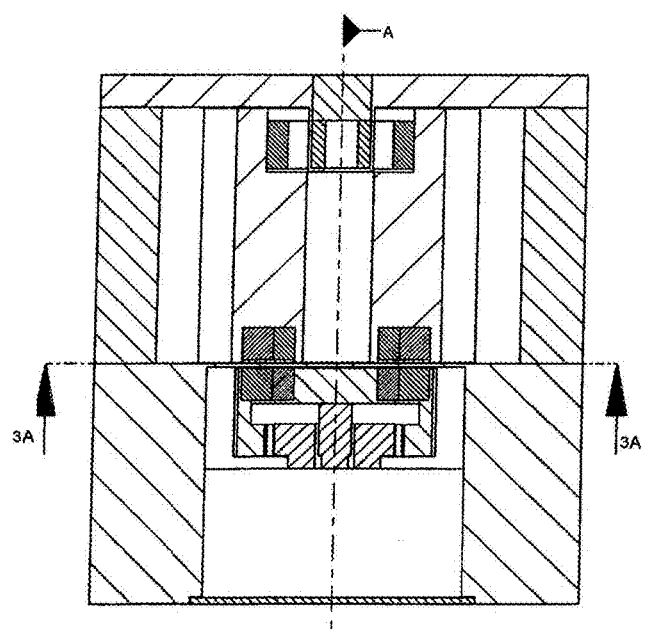
FIGS. 3B and 3C are sections taken along respective lines 3B-3B and 3C-3C of FIG. 3A.
Figure 3C:
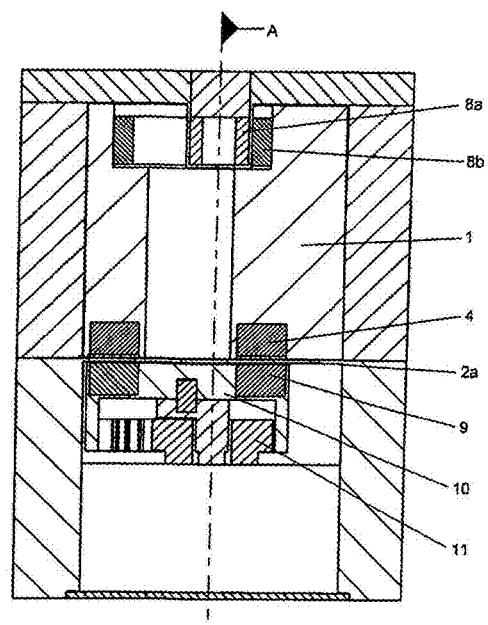
Figure 4A:
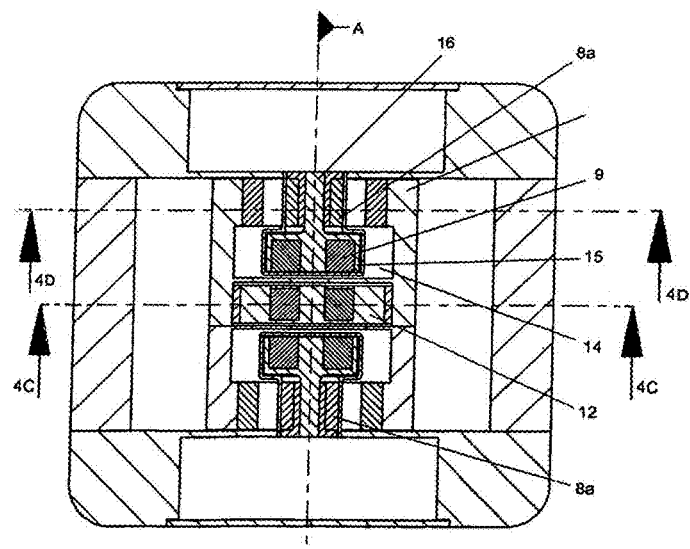
FIG. 4A is a section taken along line 4A-4A of FIG. 4C.
Figure 4B:
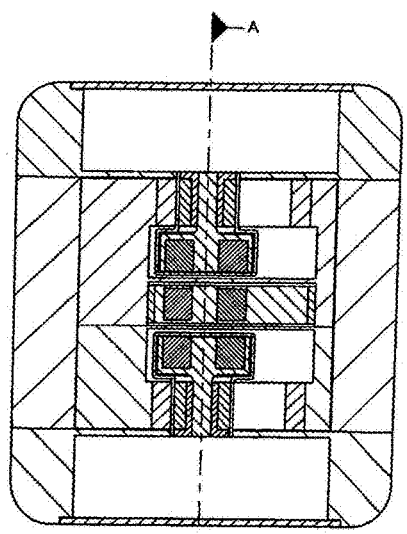
FIG. 4B is a section taken along line 4B-4B of FIG. 4D.
Figure 4C:
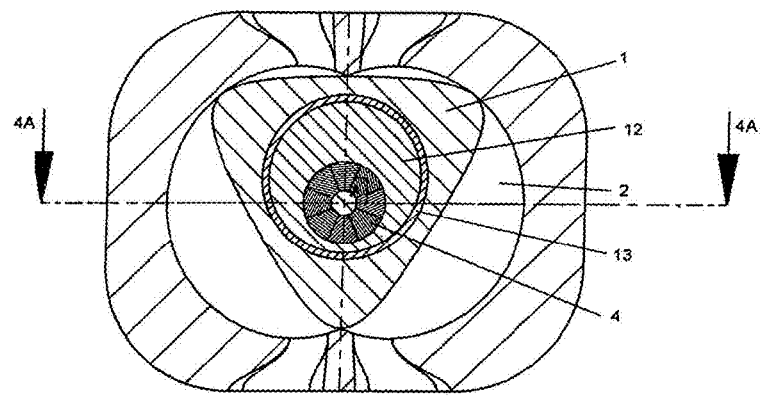
FIGS. 4C and 4D are sections taken along respective lines 4C-4C and 4D-4D of FIG. 4A.
Figure 4D:
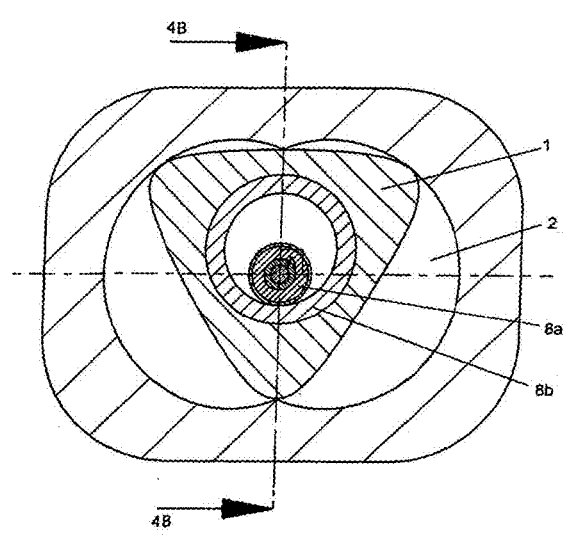

FIGS. 3A-C show another embodiment in which, with reference to FIG. 3A, shows a magnetic support with an inner first magnetic or at least magnetizable ring 8a and an outer second magnetic or at least magnetizable ring 8b and the magnetic drive is at the axially opposite end, i.e. in this case the bottom end, for which purpose the piston rotor 1 once again has magnetically attractable elements 4 such as permanent magnets on its axial end face.

Positioned spaced axially from and outside the piston chamber 2, there is a rotor that supports permanent magnets 9 whose positioning relative to one another corresponds to that of the magnetically attractable elements 4 of the piston rotor 1 so that each magnetically attractable element 4 of the piston rotor is associated with a permanent magnet of the rotor.

The rotor 10 in this case can be rotated eccentrically relative to the central axis A of the piston chamber so that the individual elements 9, in particular the permanent magnets, thus have an eccentrically rotated trajectory and thus cause the piston rotor with its elements 4 to move along with them on the same path. Therefore in this case as well, the piston rotor 1 also executes an eccentric rotation, which is also forcibly guided by the magnetic support with the rings 8a and 8b that have the same eccentricity in the support as the elements 9 of the rotor 10.

In this case, the rotor 10 can be guided on an eccentric trajectory by gears 11. The gears, for example, can form a ring gear train or planetary gear train. The rotor can be driven by a conventional electric motor; it is clear from the drawing that all of the components of the rotor are outside the piston chamber 2 and the piston rotor 1 is driven by magnetic interaction through the piston chamber wall 2a at the axial end face.

In the embodiment according to FIGS. 3A-C, the magnetically attractable elements 4 of the piston rotor 1 are stationary relative to the piston rotor.

By contrast with this, FIGS. 4A-D show an arrangement in which the magnetically attractable elements 4 in the form of circularly positioned permanent magnets or alternatively in the form of a permanent magnet ring in the piston rotor are positioned centrally around the central axis A, these elements being accommodated by a circular eccentric 12 rotationally supported in the piston rotor 1 by a support 13 that surrounds the eccentric 12. The rotation of the piston rotor 1 on an eccentric trajectory in this case occurs due to the fact that as a result of magnetic interaction between a rotor that is rotated centrally about the piston chamber central axis A, with permanent magnets, the permanent magnets 4 of the eccentric 12 are rotated centrally, which causes the eccentric 12 to rotate about the central axis A of the piston chamber 2, and, because of the inherent eccentricity of the piston rotor 1, forces the latter to follow an eccentric trajectory in the piston chamber.

The embodiment here is also designed in such a way that the eccentric 12 is positioned centrally in the piston rotor 1 relative to the central axis A and the axial length of the piston rotor 1, with inner recesses 14 being provided on both sides of the middle inside the piston rotor, in which recesses rotors 15 are positioned that rotate about the central axis A and have magnetically attractable elements 9, in particular permanent magnets, positioned around the central axis A. In this case, the shaft 16 of the rotors 15 is inserted through an inner ring 8a of a magnetic eccentric support, as has already been described in relation to the above-mentioned figures.

The depiction of the axial end face section in FIGS. 4A-D here shows that the inner ring surface of the outer magnetic ring 8b rolls along the outer ring surface of the inner centrally supported magnetic ring 8a so that, the eccentric motion of the piston rotor 1 is furthermore forcibly guided by this rolling motion. An annular intermediate element can be positioned between the rings or else at least one ring can support a coating, which can apply generally to all of the possible embodiments with such a magnetic ring support and not just to the embodiment shown here.

It should also be noted that in order to embody the magnetic support in all of the above-described figures, it is only necessary for one of the two above-mentioned rings to be magnetic whereas the other ring only has to be magnetizable. Alternatively, it is naturally also possible for both to be magnetic. The magnetizations of the rings here can be radial, axial, or in some other way so that an attracting interaction is produced between these rings as they roll against each other.

The invention claimed is:

1. A rotary-piston pump for supplying blood, the pump comprising:
    a stator housing forming a piston chamber having a central axis and a housing end wall;
    a trochoidal piston rotor having two or three lobes as seen in cross-section, rotatable eccentrically of the axis in the piston chamber, and having an axial end face juxtaposed axially with the housing end wall;
    a plurality of magnetically attractable elements in the piston rotor at the axial end face; and
    a plurality of coils on the housing end wall outside the chamber, for, on rotation of the rotor relative to the housing, generating at least one moving magnetic field effective through the housing end wall for rotationally driving the rotor solely by magnetic interaction, the coils being positioned in accordance with an envelope of the trochoidal rotor.

2. The rotary-piston pump according to claim 1, further comprising, behind the end wall,
    a plurality of permanent magnets spaced axially from the magnetically attractable elements of the piston rotor on the rotor.

3. The rotary-piston pump according to claim 1, wherein the piston rotor is magnetically supported in an eccentrically rotatable fashion on at least one of its axial end faces.

4. The rotary-piston pump according to claim 1, wherein a plurality of permanent magnets forms the magnetically attractable elements of the piston rotor or a plurality of permanent magnets forms the magnetically attractable elements of the piston rotor and is composed of a permanent magnet ring that is multiply magnetized in alternating fashion angularly.

* * * * *